US006822000B2

(12) United States Patent
Ng et al.

(10) Patent No.: US 6,822,000 B2
(45) Date of Patent: Nov. 23, 2004

(54) BIOERODIBLE POLY (ORTHOESTERS) FROM DIOXOLANE-BASED DIKETENE ACETALS

(75) Inventors: Steven Y. Ng, San Francisco, CA (US); Jorge Heller, Woodside, CA (US)

(73) Assignee: AP Pharma, Inc., Redwood City, CA (US)

(*) Notice: Subject to any disclaimer, the term of this patent is extended or adjusted under 35 U.S.C. 154(b) by 60 days.

(21) Appl. No.: 10/330,781

(22) Filed: Dec. 24, 2002

(65) Prior Publication Data

US 2003/0130472 A1 Jul. 10, 2003

Related U.S. Application Data

(62) Division of application No. 09/854,436, filed on May 11, 2001, now Pat. No. 6,590,059.

(51) Int. Cl.[7] .......................... A61K 31/335; A61F 2/00
(52) U.S. Cl. .................. 514/510; 424/426; 424/451; 424/457; 424/459; 424/78.02; 424/78.05; 514/2; 514/449; 514/506
(58) Field of Search ........................ 424/78.02, 78.05, 424/426, 451, 457, 459; 514/2, 449, 506, 510

(56) References Cited

U.S. PATENT DOCUMENTS

| | | | |
|---|---|---|---|
| 3,268,550 A | 8/1966 | Heller | 260/315 |
| 4,014,987 A | 3/1977 | Heller et al. | 424/432 |
| 4,079,038 A | 3/1978 | Choi et al. | 260/47 XA |
| 4,093,709 A | 6/1978 | Choi et al. | 424/19 |
| 4,131,648 A | 12/1978 | Choi et al. | 424/22 |
| 4,131,662 A | 12/1978 | Cekoric et al. | 264/51 |
| 4,138,344 A | 2/1979 | Choi et al. | 252/1 |
| 4,180,064 A | 12/1979 | Heller et al. | 128/833 |
| 4,180,646 A | 12/1979 | Choi et al. | 528/153 |
| 4,249,531 A | 2/1981 | Heller et al. | 424/426 |
| 4,261,969 A | 4/1981 | Heller | 424/433 |
| 4,304,767 A | 12/1981 | Heller et al. | 424/78 |
| 4,502,976 A | 3/1985 | Heller | 516/108 |
| 4,513,143 A | 4/1985 | Ng et al. | 549/335 |
| 4,532,335 A | 7/1985 | Helwing | 549/335 |
| 4,548,990 A | 10/1985 | Mueller et al. | 525/123 |
| 4,549,010 A | 10/1985 | Sparer et al. | 528/361 |
| 4,590,190 A | 5/1986 | Saito et al. | 514/221 |
| 4,605,670 A | 8/1986 | Saito et al. | 514/619 |
| 4,639,366 A | 1/1987 | Heller | 424/484 |
| 4,690,682 A | 9/1987 | Lim | 604/891 |
| 4,690,825 A | 9/1987 | Won | 424/501 |
| 4,710,497 A | 12/1987 | Heller et al. | 514/221 |
| 4,713,441 A | 12/1987 | Heller et al. | 528/392 |
| 4,738,932 A | 4/1988 | Yabusaki | 436/511 |
| 4,745,160 A | 5/1988 | Churchill et al. | 525/419 |
| 4,752,612 A | 6/1988 | Saito et al. | 514/420 |
| 4,764,364 A | 8/1988 | Heller et al. | 514/772.7 |
| 4,765,973 A | 8/1988 | Heller | 424/486 |
| 4,801,457 A | 1/1989 | Heller et al. | 424/422 |
| 4,806,360 A | 2/1989 | Leong et al. | 424/487 |
| 4,818,542 A | 4/1989 | DeLuca et al. | 424/491 |
| 4,849,426 A | 7/1989 | Pearlman | 514/274 |
| 4,855,132 A | 8/1989 | Heller et al. | 424/94.61 |
| 4,855,144 A | 8/1989 | Leong et al. | 424/487 |
| 4,898,928 A | 2/1990 | Heller et al. | 528/392 |
| 4,923,645 A | 5/1990 | Tsang et al. | 264/4.3 |
| 4,938,763 A | 7/1990 | Dunn et al. | 604/891.1 |
| 4,946,931 A | 8/1990 | Heller et al. | 528/230 |
| 4,957,998 A | 9/1990 | Heller et al. | 528/220 |
| 4,963,369 A | 10/1990 | Song et al. | 426/5 |
| 5,013,553 A | 5/1991 | Southard et al. | 424/426 |
| 5,013,821 A | 5/1991 | Heller et al. | 528/376 |
| 5,028,435 A | 7/1991 | Katz et al. | 424/484 |
| 5,030,457 A | 7/1991 | Ng et al. | 424/486 |
| 5,047,464 A | 9/1991 | Pogany et al. | 524/500 |
| 5,077,049 A | 12/1991 | Dunn et al. | 424/426 |
| 5,108,755 A | 4/1992 | Daniels et al. | 424/426 |
| 5,128,376 A | 7/1992 | Saito et al. | 514/772 |
| 5,135,740 A | 8/1992 | Katz et al. | 424/401 |
| 5,145,675 A | 9/1992 | Won | 424/78.31 |
| 5,188,844 A | 2/1993 | Ahene et al. | 424/574 |
| 5,217,712 A | 6/1993 | Pogany et al. | 424/78.18 |
| 5,240,715 A | 8/1993 | Ahene et al. | 424/574 |
| 5,256,400 A | 10/1993 | Froix et al. | 424/45 |
| 5,261,169 A | 11/1993 | Williford | 36/43 |
| 5,278,201 A | 1/1994 | Dunn et al. | 523/113 |
| 5,316,774 A | 5/1994 | Eury et al. | 424/501 |
| 5,324,519 A | 6/1994 | Dunn et al. | 424/426 |
| 5,324,520 A | 6/1994 | Dunn et al. | 424/435 |
| 5,334,640 A | 8/1994 | Desai et al. | 524/56 |
| 5,336,505 A | 8/1994 | Ng et al. | 424/486 |
| 5,340,849 A | 8/1994 | Dunn et al. | 523/113 |
| 5,368,859 A | 11/1994 | Dunn et al. | 424/426 |
| 5,407,609 A | 4/1995 | Tice et al. | 264/46 |
| 5,422,121 A | 6/1995 | Lehmann et al. | 424/464 |
| 5,449,670 A | 9/1995 | Skinner et al. | 514/3 |
| 5,458,890 A | 10/1995 | Williford et al. | 426/3 |

(List continued on next page.)

FOREIGN PATENT DOCUMENTS

| | | |
|---|---|---|
| DE | 0291668 | 7/1991 |
| DE | 4415204 | 11/1995 |
| EP | 0322392 | 6/1989 |

(List continued on next page.)

OTHER PUBLICATIONS

Andriano et al., "Preliminary effects of in vitro lipid exposure on absorbable poly(ortho ester) films," *J Appl Biomater.* 6(2): 129–35 (1995).

(List continued on next page.)

Primary Examiner—Samuel A. Acquah
(74) Attorney, Agent, or Firm—Heller Ehrman White & McAuliffe LLP

(57) ABSTRACT

Bioerodible poly(orthoesters) useful as orthopedic implants or vehicles for the sustained delivery of pharmaceutical, cosmetic and agricultural agents contain hydrogen bonding groups and α-hydroxy acid-containing groups.

20 Claims, No Drawings

U.S. PATENT DOCUMENTS

| | | | |
|---|---|---|---|
| 5,461,140 A | 10/1995 | Heller et al. | 528/425 |
| 5,487,897 A | 1/1996 | Polson et al. | 424/426 |
| 5,505,966 A | 4/1996 | Edman et al. | 424/493 |
| 5,510,116 A | 4/1996 | Froix et al. | 424/486 |
| 5,518,730 A | 5/1996 | Fuisz | 424/426 |
| 5,525,634 A | 6/1996 | Sintov et al. | 514/777 |
| 5,540,912 A | 7/1996 | Roorda et al. | 424/422 |
| 5,599,552 A | 2/1997 | Dunn et al. | 424/423 |
| 5,605,933 A | 2/1997 | Duffy et al. | 514/557 |
| 5,607,686 A | 3/1997 | Totakura et al. | 424/426 |
| 5,620,697 A | 4/1997 | Tormala et al. | 424/426 |
| 5,627,187 A | 5/1997 | Katz | 514/274 |
| 5,632,727 A | 5/1997 | Tipton et al. | 602/47 |
| 5,660,849 A | 8/1997 | Polson et al. | 424/426 |
| 5,681,873 A | 10/1997 | Norton et al. | 523/115 |
| 5,702,716 A | 12/1997 | Dunn et al. | 424/422 |
| 5,725,491 A | 3/1998 | Tipton et al. | 602/43 |
| 5,733,950 A | 3/1998 | Dunn et al. | 523/113 |
| 5,739,176 A | 4/1998 | Dunn et al. | 523/113 |
| 5,744,153 A | 4/1998 | Yewey et al. | 424/426 |
| 5,759,563 A | 6/1998 | Yewey et al. | 424/426 |
| 5,780,044 A | 7/1998 | Yewey et al. | 424/426 |
| 5,783,205 A | 7/1998 | Berggren et al. | 424/426 |
| 5,792,469 A | 8/1998 | Tipton et al. | 424/422 |
| 5,824,343 A | 10/1998 | Ng et al. | 424/486 |
| 5,837,228 A | 11/1998 | Shih et al. | 424/78.37 |
| 5,840,293 A | 11/1998 | Nacht et al. | 424/78.02 |
| 5,849,327 A | 12/1998 | Berliner et al. | 424/463 |
| 5,851,538 A | 12/1998 | Froix et al. | 424/401 |
| 5,871,722 A | 2/1999 | Nacht et al. | 424/78.03 |
| 5,879,716 A | 3/1999 | Katz et al. | 424/501 |
| 5,891,470 A | 4/1999 | Rinaldi et al. | 424/451 |
| 5,916,597 A | 6/1999 | Lee et al. | 424/501 |
| 5,939,453 A | 8/1999 | Heller et al. | 514/452 |
| 5,945,115 A | 8/1999 | Dunn et al. | 424/422 |
| 5,955,109 A | 9/1999 | Won et al. | 424/501 |
| 5,968,543 A | 10/1999 | Heller et al. | 424/425 |
| 5,990,194 A | 11/1999 | Dunn et al. | 523/113 |
| 5,993,856 A | 11/1999 | Ragavan et al. | 424/489 |
| 6,007,845 A | 12/1999 | Domb et al. | 424/501 |
| 6,046,187 A | 4/2000 | Berde et al. | 514/180 |
| 6,071,530 A | 6/2000 | Polson et al. | 424/426 |
| 6,083,521 A | 7/2000 | Acemoglu et al. | 424/422 |
| 6,096,344 A | 8/2000 | Liu et al. | 424/501 |
| 6,143,314 A | 11/2000 | Chandrashekar et al. | 424/426 |
| 6,159,491 A | 12/2000 | Durrani | 424/430 |
| 6,166,173 A | 12/2000 | Mao et al. | 528/398 |
| 6,193,991 B1 | 2/2001 | Shukla | 424/426 |
| 6,206,920 B1 | 3/2001 | Eliaz et al. | 623/16.11 |
| 6,217,895 B1 | 4/2001 | Guo et al. | 424/427 |
| 6,238,705 B1 | 5/2001 | Liu et al. | 424/501 |
| 6,245,345 B1 | 6/2001 | Swanborn et al. | 424/402 |
| 6,261,583 B1 | 7/2001 | Dunn et al. | 424/422 |
| 6,262,127 B1 | 7/2001 | Acemoglu et al. | 514/772.7 |
| 6,281,015 B1 | 8/2001 | Mooney et al. | 435/395 |
| 6,287,588 B1 | 9/2001 | Shih et al. | 424/426 |
| 6,331,311 B1 | 12/2001 | Brodbeck et al. | 424/425 |
| 6,372,245 B1 | 4/2002 | Bowman et al. | 424/427 |
| 6,395,293 B2 | 5/2002 | Polson et al. | 424/426 |
| 6,524,606 B1 | 2/2003 | Ng et al. | 424/425 |
| 6,590,059 B2 | 7/2003 | Ng et al. | 528/220 |
| 6,613,355 B2 | 9/2003 | Ng et al. | 424/462 |
| 2002/0037300 A1 | 3/2002 | Ng et al. | 424/401 |
| 2002/0082362 A1 | 6/2002 | Brocchini et al. | 525/461 |
| 2002/0090398 A1 | 7/2002 | Dunn et al. | 424/486 |
| 2002/0168336 A1 | 11/2002 | Ng et al. | 424/78.38 |
| 2002/0176844 A1 | 11/2002 | Ng et al. | 424/78.38 |
| 2003/0130472 A1 | 7/2003 | Ng et al. | 528/73 |
| 2003/0138474 A1 | 7/2003 | Ng et al. | 424/425 |
| 2003/0152630 A1 | 8/2003 | Ng et al. | 424/486 |

FOREIGN PATENT DOCUMENTS

| | | |
|---|---|---|
| EP | 0419156 | 3/1991 |
| EP | 0466566 | 1/1992 |
| EP | 0485840 | 5/1992 |
| EP | 0524831 | 1/1993 |
| EP | 0471036 | 1/1996 |
| EP | 1142596 | 10/2001 |
| FR | 2238477 | 2/1975 |
| FR | 2352547 | 12/1977 |
| GB | 1482663 | 8/1977 |
| GB | 1579490 | 11/1980 |
| JP | 2218719 | 8/1990 |
| JP | 3000732 | 1/1991 |
| JP | 3005419 | 1/1991 |
| WO | 8703692 | 6/1987 |
| WO | 8801164 | 2/1988 |
| WO | 8910132 | 11/1989 |
| WO | 8910818 | 11/1989 |
| WO | 8910947 | 11/1989 |
| WO | 9012605 | 11/1990 |
| WO | 9013361 | 11/1990 |
| WO | 9103510 | 3/1991 |
| WO | 9104732 | 4/1991 |
| WO | 9107101 | 5/1991 |
| WO | 9117738 | 11/1991 |
| WO | 9200732 | 1/1992 |
| WO | 9218222 | 1/1992 |
| WO | 9202210 | 2/1992 |
| WO | 9300383 | 1/1993 |
| WO | 9306757 | 4/1993 |
| WO | 9307862 | 4/1993 |
| WO | 9310826 | 6/1993 |
| WO | 9325077 | 12/1993 |
| WO | 9414417 | 7/1994 |
| WO | 9516659 | 6/1995 |
| WO | 9632419 | 10/1996 |
| WO | 9720812 | 6/1997 |
| WO | 9725980 | 7/1997 |
| WO | 9727843 | 8/1997 |
| WO | 9739746 | 10/1997 |
| WO | 9953904 | 10/1999 |
| WO | 9962983 | 12/1999 |
| WO | 0000159 | 1/2000 |
| WO | 0115734 | 3/2001 |
| WO | 0135929 | 5/2001 |
| WO | 0174411 | 10/2001 |
| WO | 0220663 | 3/2002 |
| WO | 0185139 | 4/2002 |
| WO | 02092061 | 11/2002 |
| WO | 02092655 | 11/2002 |
| WO | 02092661 | 11/2002 |
| WO | 03044446 | 5/2003 |

OTHER PUBLICATIONS

Andriano et al., "Biocompatibility and mechanical properties of a totally absorbable composite material for orthopaedic fixation devices", *J Appl Biomater.*, 3(3):197–206 (1992).

Ashford et al., "An evaluation of pectin as a carrier for drug targeting to the colon," *Chemical Abstracts* 119:278554r (1993) pp. 514.

Barr et al. "Post surgical pain management with poly(ortho esters)," *Adv Drug Deliv Rev.* 54(7):1041–8 (2002).

Bernatchez et al. "Biotolerance of a semisolid hydrophobic biodegradable poly(ortho ester) for controlled drug delivery," *J Biomed Mater Res.* 27(5):677–81 (1993).

Beyerstedt et al., "The Preparation And Properties of Ketene Diethylacetal", J. Amer. Chem. Soc., 58, 529–531 (1936).

Castillo et al. "*Glucocorticoids Prolong Rat Sciatic Nerve Blockade*In Vivo from *Bupivacine Microspheres,*" *Anesthesiology* 85(3):1157–1166 (1996).

Chia et al. "Auto–catalyzed poly(ortho ester) microspheres: a study of their erosion and drug release mechanism," *J Control Release.* 75(1–2):11–25 (2001).

*Contemporary Polymer Chemistry 3rd Ed.* Allcock et al. (eds.) *Upper Saddle River, New Jersey: Pearson Education, Inc.* Ch. 1 pp. 11–12 (2003).

Corey et al., "Selective Cleavage of Allyl Ethers under Mild Conditions by Transition Metal Regents", *J. Org. Chem.,* 38(18):3224 (1973).

Dahl JB et al. "Wound inflation with local anaesthetics for postoperative pain relief", *Acta Anaesthesiol Scand* 38:7–14 (1994).

Daniels et al., "Evaluation of absorbable poly(ortho esters) for use in surgical implants", *J Appl Biomater.*, 5(1):51–64 (1994).

Derwent Abstract, Accession No 10473386 for German Patent Application DE 4415204 published Nov. 2, 1995, "Compsns contg retinyl salicylate or acetyl–salicylate—for pharmaceutical or cosmetic treatment of inflammation, general necrosis, intoxication, allergies, tumours, etc.".

Derwent Abstract, Accession No. 15388893 for PCT Patent Publication WO 200344446 published May 30, 2003, "Disposal of materials containing high–energy substances, especially shells, comprises recycling bulk material leaving a fluidized bed in a non–cooled state to a different inlet region than the materials for disposal".

Derwent Abstract, Accession No. 8850667 for German Patent Application DD 291668 A published Jul. 11, 1991, "GnRH prepn. for oral use—consist of GNRH nucleus contg. detergent to promote resorption, inner coating which dissolves in the colon and outer coating".

Derwent Abstract, Accession No. 3209328 for Japanese Patent Applications JP 2218719 published Aug. 31, 1990 and JP 300732 published Jan. 7, 1991, "Biodegradable polymers from polyol and ketene acetal—useful for making implants for delivering pharmaceuticals et al."

Derwent Abstract, Accession No. 8469383 for Japanese Patent application 3005419 published Jan. 11, 1991, "New percutaneous rate controlled delivery system—comprising drug, penetration enhancer and polymeric particles in a matrix layer".

Deshpande et al. "Bioerodible polymers for ocular drug delivery," *Crit Rev Ther Drug Carrier Syst.* 15(4):381–420 (1998).

Dräger et al., "Prolonged Intercostal Nerve Blockade in Sheep Using Controlled–release of Bupivacaine and Dexamethasone from Polymer Microspheres," *Anesthesiology* 89(4):969–979 (1998).

Duenas et al., "Sustained Delivery of rhVEGF from a Novel injectable Liquid, PLAD," *Proceed. Int'l Control Rel. Bioact. Mater.* 28:1041–1042 (2001).

Einmahl et al., "A viscous bioerodible poly(ortho ester) as a new biomaterial for intraocular application," *J Biomed Mater Res.* 50(4):566–73 (2000).

Einmahl et al., "Concomitant and controlled release of dexamethasone and 5–fluorouracil from poly(ortho ester)," *Int J Pharm*, 185(2):189–98 (1999).

Einmahl et al., "Ocular biocompatibility of a poly(ortho ester) characterized by autocatalyzed degradation", *J. Biomed Mater Res.*, 67A(1):44–53 (2003).

Geary et al., "Vancomycin and insulin used as models for oral delivery of peptides," *J of Controlled Release* 23:65–74 (1993).

Heller et al., "Controlled drug release from bioerodible hydrophobic ointments," *Biomaterials.* 11(4):235–7 (1990).

Heller et al., "Controlled release of water–soluble macromolecules from bioerodible hydrogels," *Biomaterials.* 4(4):262–6 (1983).

Heller et al., "Poly(ortho ester) biodegradable polymer systems," *Methods Enzymol.* 112:422–36 (1985).

Heller et al. "Controlled release of contraceptive steroids from biodegradable poly (ortho esters)," Contracept Deliv Syst. 4(1):43–53 (1983).

Heller et al. Erratum to "Poly(ortho esters)—their development and some recent applications," *Eur J Pharm Biopharm.* 50(1):121–8. (2000) Review. Erratum in: Eur J Pharm Biopharm Sep. 2000;50(2):327.

Heller J., "Controlled drug release from poly(ortho esters)," *Ann N Y Acad Sci.*, 446:51–66 (1985).

Heller J., "Modulated release from drug delivery devices," *Crit Rev Ther Drug Carrier Syst.* 10(3):253–305 (1993).

Heller J., "Preparation of Polyacetals by the Reaction of Divinyl Ethers and Polyols"; J. Polymer Sci. Polymer Letters Ed., 18,293–297 (1980).

Heller et al., "Development of poly(ortho esters) and their application for bovine serum albumin and bupivacaine delivery", *J Control Release*, 78(1–3): 133–141 (2002).

Heller, J. "Development of poly(ortho esters): a historical overview", *Biomaterials*, 11(9):659–65 (1990).

Kipper et al., "Design of an Injectable system based on bioerodible polyanhydride microspheres for sustained drug delivery" *Biomaterials* 23:4405–4412 (2002).

Leadley et al., "The use of SIMS, XPS and in situ AFM to probe the acid catalysed hydrolysis of poly(orthoesters)," *Biomaterials.* 19(15):1353–60 (1998).

Merkli et al., "Synthesis and characterization of a new biodegradable semi–solid poly(ortho ester) for drug delivery systems," *J Biomater Sci Polym Ed.* 4(5):505–16 (1993).

Merkli et al., "Gamma sterilization of a semi–solid poly-(ortho ester) designed for controlled drug delivery—validation and radiation effects," *Pharm Res.* 11(10):1485–91 (1994).

Merkli et al., "Purity and stability assessment of a semi–solid poly(ortho ester) used in drug delivery systems," *Biomaterials.* 17(9):897–902 (1996).

Milojevic et al., "Amylose as a coating for drug delivery to the colon: preparation and vitro evaluation using 5–aminosalicylic acid pellets," *J of Controlled Release* 38:75–84 (1996).

Okumu et al., "Sustained Delivery of Growth Hormones from a Novel Injectable Liquid, PLAD," *Proceed. Int'l Symp. Control Rel. Bioact. Mater.* 28:1029–1030 (2001).

Press Release: "Advanced Polymer Systems Granted Two Composition of Matter Patents Related to its Bioerodible Polymer Technology," Advanced Polymer Systems News Release, Oct. 1999.

Roberts et al., "The Role of Neighboring Groups in Replacement Reactions.", J. Amer. Chem. Soc., 80:1247–1254 (1958).

Roskos et al., "Development of a drug delivery system for the treatment of periodontal disease based on bioerodible poly(ortho esters)," *Biomaterials*, 16(4):313–7 (1995).

Rothen–Weinhold et al., "Release of BSA from poly(ortho ester) extruded thin strands," *J Control Release*, 71(1):31–7 (2001).

Schwach–Abdellaoui et al., "Optimization of a novel bio-erodible device based on auto–catalyzed poly(ortho esters) for controlled delivery of tetracycline to periodontal pocket," *Biomaterials*. 22(12):1659–66 (2001).

Schwach–Abdellaoui et al., "Bioerodible injectable poly-(ortho ester) for tetracycline controlled delivery to periodontal pockets: preliminary trial in humans," *AAPS PharmSci*. 4(4):article 20 pp. 1–7 (2002).

Schwach–Abdellaoui et al., "Synthesis and characterization of self–catalyzed poly(ortho–esters) based on decanediol and decanediol–lactate," *J Biomater Sci Polym Ed.* 10(3):375–89 (1999).

Shi et al., "Double walled POE/PLGA microspheres: encapsulation of water–soluble and water–insoluble proteins and their release properties," *J Control Release*. 89(2):167–77 (2003).

Sintzel et al., "In vitro drug release from self–catalyzed poly(ortho ester): case study of 5–fluorouracil," *J Control Release*. 55(2–3):213–8 (1998).

Sintzel et al., "Synthesis and characterization of self–catalyzed poly(ortho ester)," *Biomaterials*. 19(7–9):791–800 (1998).

Steinicke A. et al. "Oral formulations of gonadotropin releasing hormone" *Chemical Abstracts* 115(22): 239759j (1991).

Taylor et al., "Six bioabsorbable polymers: in vitro acute toxicity of accumulated degradation products," *J Appl Biomater*. 5(2):151–7 (1994).

*Textbook of Polymer Science 3rd Ed.* Billmeyer, F.W. (ed.) New York: John Wiley & Sons Ch. 17 pp. 457–485 (1984).

Tomlinson et al. "Polyacetal–doxorubicin conjugates designed for pH–dependent degradation", *Bioconjug Chem.*, 14(6):1096–1106 (2003).

Uyeda, C.T., "Agglutination of Cardiolipin–Coated Latex Particles with VDRL– And Kolmer–Positive Serums," *American Journal of Clinical Pathology* 40:329–333 (1963).

van de Weert et al., "Semi–solid self–catalyzed poly(ortho ester)s as controlled–release systems: protein release and protein stability issues," *J Pharm Sci.*91(4):1065–74 (2002).

Wan et al.., "POE–PEG–POE triblock copolymeric microspheres containing protein. II. Polymer erosion and protein release mechanism," *J Control Release*. 75(1–2):129–41 (2001).

Yang et al. "POE/PLGA composite microspheres: formation and in vitro behavior of double walled microspheres," *J Control Release*. 88(2):201–13 (2003).

Yang et al. "POE–PEG–POE triblock copolymeric microspheres containing protein. I. Preparation and characterization," *J Control Release*. 75(1–2):115–28 (2001).

Zignani et al., "A poly(ortho ester) designed for combined ocular delivery of dexamethasone sodium phosphate and 5–fluorouracil: subconjunctival tolerance and in vitro release," *Eur J Pharm Biopharm*. 50(2):251–5 (2000).

Zignani et al., "Improved biocampatibility of a viscous bioerodible poly(ortho ester) by controlling the environmental pH during degradation," *Biomaterials* 21(17):1773–8 (2000).

J. Heller et al., "Preparation Of Polyacetals By The Reaction Of Divinyl Ethers and Polyols", *J. Polymer Sci., Polymer Letters Ed.*, 18, 293 297 (1980).

J. Crivello, "Ketene Acetal Monomers: Synthesis and Characterization", *J. Polymer Sci. Part A: Polymer Chemistry*, 34, 3091–3192 (1996).

"Semi–solid delivery vehicle and pharmaceutical compositions", US Patent Application No. 09/854,180, filed May 11, 2001.

Heller et al. "Controlled drug release by polymer dissolution. II: Enzyme–mediated delivery device," *J Pharm Sci.*, 68(7):919–921 (1979).

Heller, J., "Controlled release of biologically active compounds from bioerodible polymers", *Biomaterials*, 1:51–57 (1980).

Heller et al, "Controlled release of contraceptive steroids from biodegradable poly (ortho esters)", *Contraceptive Delivery Systems*, 4(1):43–53 (1983).

Heller et al., "Controlled release of water–soluble macromolecules from bioerodible hydrogels",*Biomaterials*, 4(4):262–6 (1983).

Heller J., "Biodegradable polymers in controlled drug delivery", *Crit Rev Ther Drug Carrier Syst.*, 1(1):39–90 (1984).

Heller J., Controlled drug release from poly(ortho esters) *Ann N Y Acad Sci.*, 446:51–66 (1985).

Heller, J. and J.K. Himmelstein, "Poly(ortho ester) Biodegradable Polymer Systems", *Methods in Enzymology*, 112:422–436 (1985).

Heller et al., "Controlled drug release from bioerodible hydrophobic ointments", *Biomaterials*, 11(4):235–7 (1990).

Heller J., "Modulated release from drug delivery devices", *Crit Ther Drug Carrier Syst*, 10(3):253–305 (1993).

Heller J., "The use of polymers in the construction of controlled–release devices", *NIDA Res Monogr*, 154:107–31 (1995).

Heller et al., "Poly(ortho esters)—their development and some recent applications", *Eur J Pharm Biopharm*, 50(1):121–128 (2000). Erratum in: *Eur J Pharm Biopharm*, 50(2):327.

Heller et al., "Poly(ortho esters): synthesis, characterization, properties and uses", *Adv Drug Deliv Rev.*, 54(7):1015–39 (2002).

Heller et al., "Development and applications of injectable poly(ortho esters) for pain control and periodontal treatment", *Biomaterials,* 23(22):4397–4404 (2002).

Ng et al., "Controlled drug release from self–catalyzed poly(ortho esters)",*Ann N Y Acad. Sci.,*831:168–178 (1997).

Ng et al., "Development of a poly(ortho ester) prototype with a latent acid in the polymer backbone for 5–fluorouracil delivery", *J Control Release*, 65:367–74 (2000).

BIOERODIBLE POLY (ORTHOESTERS) FROM DIOXOLANE-BASED DIKETENE ACETALS

CROSS-REFERENCE TO RELATED APPLICATION

This application is a divisional of application Ser. No. 09/854,436, filed May 11, 2001 now U.S. Pat. No. 6,590,059, which is incorporated into this application by reference.

BACKGROUND OF THE INVENTION

1. Field of the Invention

This application relates to poly(orthoesters). In particular, this invention relates to bioerodible poly(orthoesters) containing new diketene acetals and α-hydroxy acid-containing groups.

2. Description of the Prior Art

Interest in synthetic biodegradable polymers for the systemic delivery of therapeutic agents began in the early 1970's with the work of Yolles et al., *Polymer News* 1, 9–15 (1970) using poly(lactic acid). Since that time, numerous other polymers have been prepared and investigated as bioerodible matrices for the controlled release of therapeutic agents.

U.S. Pat. Nos. 4,079,038, 4,093,709, 4,131,648, 4,138,344 and 4,180,646 disclose biodegradable or bioerodible poly(orthoesters). These polymers are formed by a reaction between an orthoester (or orthocarbonate) such as 2,2-diethoxytetrahydrofuran and a diol such as 1,4-cyclohexanedimethanol. The reaction requires elevated temperature and reduced pressure and a relatively long reaction time. Drugs or other active agents are retained in the polymer matrix to be released as the polymer biodegrades due to hydrolysis of the labile linkages.

U.S. Pat. No. 4,304,767 discloses polymers prepared by reacting a polyol with a polyfunctional ketene acetal. These polymers represent a significant improvement over those of U.S. Pat. Nos. 4,079,038, 4,093,709, 4,131,648, 4,138,344 and 4,180,646, since synthesis proceeds readily at room temperature and atmospheric pressure, and the resulting polymers have superior properties.

Further polymers are disclosed in U.S. Pat. No. 4,957,998. These polymers contain acetal, carboxy-acetal and carboxy-orthoester linkages, and are prepared by a two-step process beginning with the reaction between a polyfunctional ketene acetal and a compound containing a vinyl ether, followed by reaction with a polyol or polyacid.

Still further polymers of a similar type are disclosed in U.S. Pat. No. 4,946,931. The polymers are formed by a reaction between a compound containing a multiplicity of carboxylate functions and a polyfunctional ketene acetal. The resulting polymers have very rapid erosion times.

Despite the ease with which the orthoester linkage hydrolyses, poly(orthoesters) known in the prior art are extremely stable materials when placed in an aqueous buffer, or when residing in the body. This stability is attributable to the extreme hydrophobicity of the poly(orthoesters) which severely limits the amount of water that can penetrate the polymer. To achieve useful erosion rates, therefore, acidic excipients must be physically incorporated into the polymer. While this allows control over erosion rates, the physically incorporated acidic excipient can diffuse from the polymer matrix at varying rates, leaving a matrix that is completely depleted of excipient while the polymer still has a very long lifetime remaining.

U.S. Pat. No. 5,968,543 (Heller et al.) describes poly(orthoesters) containing α-hydroxy acid-containing groups. The poly(orthoesters) are formed from the reaction of a diketene acetal such as 3,9-di(ethylidene)-2,4,8,10-tetraoxaspiro[5.5]undecane (DETOSU) with at least 0.1 mol % of an "α-hydroxy acid" diol and 0–99.9 mol % of one or more of a "hard" diol and a "soft" diol (as those terms are used in the patent). These poly(orthoesters) are stated to have greater bioerodibility than similar poly(orthoesters) not containing the α-hydroxy acid ester-containing groups, and to have the bioerodibility controllable by variation in the concentration of the α-hydroxy acid ester-containing groups.

U.S. Pat. No. 4,549,010 (Sparer et al.) describes poly(orthoesters) containing functional groups which produce hydrogen bonding.

The disclosures of the documents listed in this section and elsewhere throughout this application are incorporated herein by reference.

SUMMARY OF THE INVENTION

In a first aspect, this invention is poly(orthoesters) of formula I:

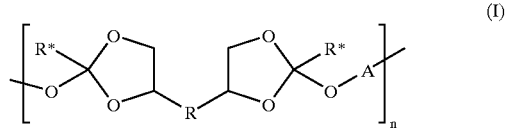

where:

R is a bond, $-(CH_2)_a-$, or $-(CH_2)_b-O-(CH_2)_c-$; where a is an integer of 1 to 10, and b and c are independently integers of 1 to 5;

$R^*$ is a $C_{1-4}$ alkyl;

n is an integer of at least 5; and

A is $R^1$, $R^2$, $R^3$, or $R^4$, where $R^1$ is:

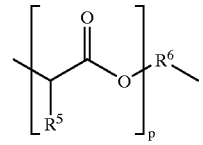

where:

p is an integer of 1 to 20;

$R^5$ is hydrogen or $C_{1-4}$ alkyl; and $R^6$ is:

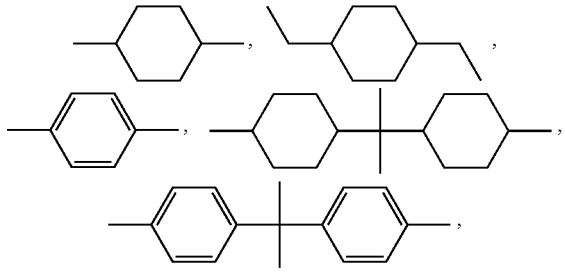

-continued

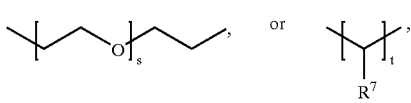

where:
s is an integer of 0 to 30;
t is an integer of 2 to 200; and
$R^7$ is hydrogen or $C_{1-4}$ alkyl;
$R^2$ is:

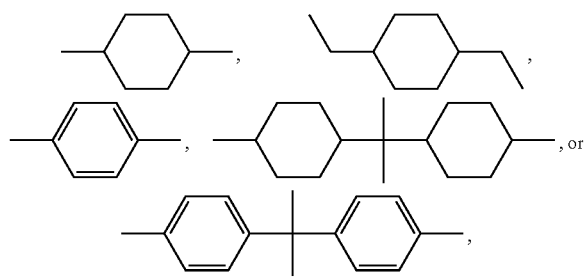

$R^3$ is:

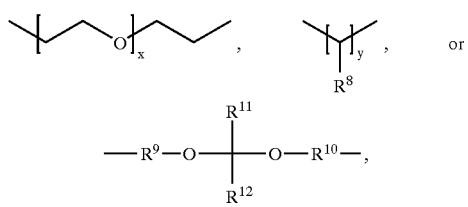

where:
x is an integer of 0 to 30;
y is an integer of 2 to 200;
$R^8$ is hydrogen or $C_{1-4}$ alkyl;
$R^9$ and $R^{10}$ are independently $C_{1-12}$ alkylene;
$R^{11}$ is hydrogen or $C_{1-6}$ alkyl and $R^{12}$ is $C_{1-6}$ alkyl; or $R^{11}$ and $R^{12}$ together are $C_{3-10}$ alkylene; and
$R^4$ is the residue of a diol containing at least one functional group independently selected from amide, imide, urea, and urethane groups;
in which at least 0.1 mol % of the A units are $R^1$.

In a second aspect, this invention is controlled release pharmaceutical compositions comprising:
(a) an active agent; and
(b) as a vehicle, the poly(orthoester) described above.

In a third aspect, this invention is a method of treating a disease state treatable by controlled release local administration of an active agent, in particular treating pain by administration of a local anesthetic or treating cancer by administration of a chemotherapeutic or antineoplastic agent, comprising locally administering a therapeutically effective amount of the active agent in the form of the pharmaceutical composition described above.

In a fourth aspect, this invention is methods of using the poly(orthoesters) of the first aspect of the invention as bioerodible implants.

In a fifth aspect, this invention is methods of preparation of the poly(orthoesters) of the first aspect of the invention and the controlled release pharmaceutical compositions of the second aspect of the invention.

DETAILED DESCRIPTION OF THE INVENTION

It has now been discovered that poly(orthoesters) useful as orthopedic implants or vehicles for the sequestration and sustained delivery of drugs, cosmetic agents and other beneficial agents can be prepared in such a manner that the rate and degree to which they are hydrolyzed by contact with bodily fluids at normal body temperature and pH can be controlled without addition of exogenous acid. This discovery resides in the incorporation of esters of short-chain 1-hydroxy acids such as esters of glycolic acid, lactic acid or glycolic-co-lactic acid copolymer into the poly(orthoester) chain and variation of the amount of these esters relative to the poly(orthoester) as a whole.

In the presence of water, these esters, when incorporated into the poly(orthoester) chain, are readily hydrolyzed at a body temperature of 37° C. and a physiological pH, in particular at a pH of 7.4, to produce the corresponding α-hydroxy acids. The α-hydroxy acids then act as an acidic excipient to control the hydrolysis rate of the poly(orthoester). When the poly(orthoester) is used as a vehicle or matrix entrapping an active agent, the hydrolysis of the poly(orthoester) causes release of the active agent.

In addition, the mechano-physical state of the poly(orthoester) may also be controlled. This is achieved by the inclusion of the residues of certain diols in selected proportions relative to the poly(orthoester) as a whole. For example, a high content of the residue of trans-1,4-cyclohexane-dimethanol or a similar "hard" diol relative to a "soft" diol (definition of which is given below) produces a relatively rigid polymer chain and a more solid substance, and by decreasing the trans-cyclohexane-dimethanol content relative to the "soft" diol, the poly(orthoester) will change progressively through the stages of a rigid thermoplastic, a soft thermoplastic, a low melting solid to an ointment-like (viscous liquid) material, and any stage in between.

The poly(orthoesters) of the present invention are prepared by condensation reactions between diketene acetals and polyols, preferably diols, and the variation in mechano-physical state and rate of hydrolysis (bioerodibility) is achieved by the selection and use of combinations of different types of diols.

Definitions

"Active agent" includes any compound or mixture of compounds which produces a beneficial or useful result. Active agents are distinguishable from such components as vehicles, carriers, diluents, lubricants, binders and other formulating aids, and encapsulating or otherwise protective components. Examples of active agents are pharmaceutical, agricultural or cosmetic agents. Suitable pharmaceutical agents include locally or systemically acting pharmaceutically active agents which may be administered to a subject by topical or intralesional application (including, for example, applying to abraded skin, lacerations, puncture wounds, etc., as well as into surgical incisions) or by injection, such as subcutaneous, intradermal, intramuscular, intraocular, or intra-articular injection. Examples of these agents include, but not limited to, anti-infectives (including antibiotics, antivirals, fungicides, scabicides or pediculicides), antiseptics (e.g., benzalkonium chloride, benzethonium chloride, chlorhexidine gluconate, mafenide acetate, methylbenzethonium chloride, nitrofurazone, nitromersol and the like), steroids (e.g., estrogens, progestins, androgens, adrenocorticoids, and the like), therapeutic polypeptides (e.g. insulin, erythropoietin, morphogenic proteins such as bone morphogenic protein, and the like), analgesics and anti-inflammatory agents (e.g., aspirin, ibuprofen, naproxen, ketorolac, COX-1 inhibitors, COX-2 inhibitors, and the like), cancer chemotherapeutic agents (e.g., mechlorethamine, cyclophosphamide, fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, tamoxifen, and the like), narcotics (e.g., morphine, meperidine, codeine, and the like), local anesthetics (e.g., the amide- or anlide-type local anesthetics such as bupivacaine, dibucaine, mepivacaine, procaine, lidocaine, tetracaine, and the like), antiangiogenic agents (e.g., combrestatin, contortrostatin, anti-VEGF, and the like), polysaccharides, vaccines, antigens, DNA and other polynucleotides, antisense oligonucleotides, and the like. The present invention may also be applied to other locally acting active agents, such as astringents, antiperspirants, irritants, rubefacients, vesicants, sclerosing agents, caustics, escharotics, keratolytic agents, sunscreens and a variety of dermatologics including hypopigmenting and antipruritic agents. The term "active agents" further includes biocides such as fungicides, pesticides, and herbicides, plant growth promoters or inhibitors, preservatives, disinfectants, air purifiers and nutrients.

"Alkyl" denotes a linear saturated hydrocarbyl having from one to the number of carbon atoms designated, or a branched or cyclic saturated hydrocarbyl having from three to the number of carbon atoms designated (e.g., $C_{1-4}$ alkyl). Examples of alkyl include methyl, ethyl, n-propyl, isopropyl, cyclopropyl, n-butyl, t-butyl, cyclopropylmethyl, and the like.

"Alkylene" denotes a branched or unbranched saturated divalent radical having from one to the number of carbon atoms designated (e.g., $C_1$–$C_{12}$ alkylene). Examples of alkylene include methylene (—$CH_2$—), ethylene (—$CH_2CH_2$—), isopentylene (—$CH_2$—$CH(CH_3)$—$CH_2$—$CH_2$—), n-octylene (—$(CH_2)_8$—) and the like.

"Bioerodible" and "bioerodibility" refer to the degradation, disassembly or digestion of the poly (orthoester) by action of a biological environment, including the action of living organisms and most notably at physiological pH and temperature. A principal mechanism for bioerosion of the poly(orthoesters) of the present invention is hydrolysis of linkages between and within the units of the poly(orthoester).

"Comprising" is an inclusive term interpreted to mean containing, embracing, covering or including the elements listed following the term, but not excluding other unrecited elements.

"Controlled release", "sustained release", and similar terms are used to denote a mode of active agent delivery that occurs when the active agent is released from the delivery vehicle at an ascertainable and controllable rate over a period of time, rather than dispersed immediately upon application or injection. Controlled or sustained release may extend for hours, days or months, and may vary as a function of numerous factors. For the pharmaceutical composition of the present invention, the rate of release will depend on the type of the excipient selected and the concentration of the excipient in the composition. Another determinant of the rate of release is the rate of hydrolysis of the linkages between and within the units of the poly(orthoester). The rate of hydrolysis in turn may be controlled by the composition of the poly(orthoester) and the number of hydrolysable bonds in the poly(orthoester). Other factors determining the rate of release of an active agent from the present pharmaceutical composition include particle size, acidity of the medium (either internal or external to the matrix) and physical and chemical properties of the active agent in the matrix.

"Matrix" denotes the physical structure of the poly (orthoester) which essentially retains the active agent in a manner preventing release of the agent until the poly (orthoester) erodes or decomposes.

"Sequestration" is the confinement or retention of an active agent within the internal spaces of a poly(orthoester) matrix. Sequestration of an active agent within the matrix may limit the toxic effect of the agent, prolong the time of action of the agent in a controlled manner, permit the release of the agent in a precisely defined location in an organism, or protect unstable agents against the action of the environment.

A "therapeutically effective amount" means the amount that, when administered to an animal for treating a disease, is sufficient to effect treatment for that disease.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

A "unit" denotes an individual segment of a poly (orthoester) chain, which consists of the residue of a diketene acetal molecule and the residue of a polyol.

An "α-hydroxy acid containing" unit denotes a unit where A is $R^1$, i.e. in which the polyol is prepared from an a-hydroxy acid or cyclic diester thereof and a diol of the formula HO—$R^6$—OH. The fraction of the poly(orthoester) that is α-hydroxy acid containing units affects the rate of hydrolysis (or bioerodibility) of the poly(orthoester), and in turn, the release rate of the active agent.

"Hard", "soft", and "hydrogen bonding" units denote individual units of the poly(orthoester), the contents of which relative to the poly(orthoester) as a whole determine the mechano-physical state of the poly(orthoester). "Hard" units are units where A is $R^2$, "soft" units are units where A is $R^3$, and "hydrogen bonding" units are units where A is $R^4$.

"Vehicle" and "carrier" denote an ingredient that is included in a composition such as a pharmaceutical or cosmetic preparation for reasons other than a therapeutic or other biological effect. Functions served by vehicles and carriers include transporting an active agent to a site of interest, controlling the rate of access to, or release of, the active agent by sequestration or other means, and facilitating the application of the agent to the region where its activity is needed.

The poly(Orthoesters)

The poly(orthoesters) are of formula I:

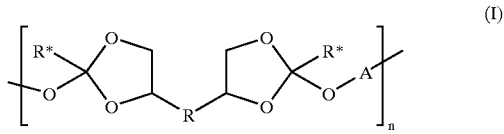

where:
R is a bond, —$(CH_2)_a$—, or —$(CH_2)_b$—O—$(CH_2)_c$—; where a is an integer of 1 to 10, and b and c are independently integers of 1 to 5;
R* is a $C_{1-4}$ alkyl;
n is an integer of at least 5; and A is $R^1$, $R^2$, $R^3$, or $R^4$, where
$R^1$ is:

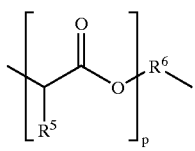

where:
  p is an integer of 1 to 20;
  $R^5$ is hydrogen or $C_{1-4}$ alkyl; and
  $R^6$ is:

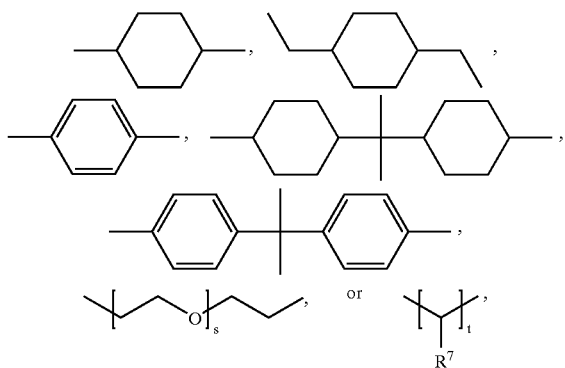

where:
  s is an integer of 0 to 30;
  t is an integer of 2 to 200; and
  $R^7$ is hydrogen or $C_{1-4}$ alkyl;
$R^2$ is:

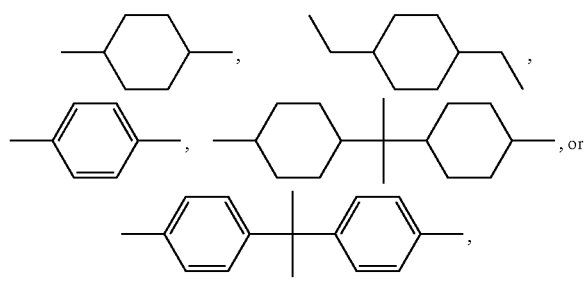

$R^3$ is:

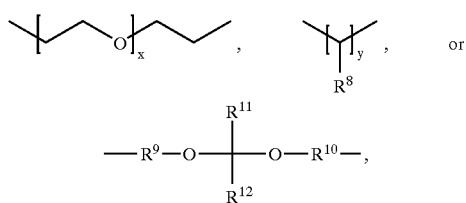

where:
  x is an integer of 0 to 30;
  y is an integer of 2 to 200;
  $R^8$ is hydrogen or $C_{1-4}$ alkyl;
  $R^9$ and $R^{10}$ are independently $C_{1-12}$ alkylene;
  $R^{11}$ is hydrogen or $C_{1-6}$ alkyl and $R^{12}$ is $C_{1-6}$ alkyl; or $R^{11}$ and $R^{12}$ together are $C_{3-10}$ alkylene; and $R^4$ is the residue of a diol containing at least one functional group independently selected from amide, imide, urea, and urethane groups;
in which at least 0.1 mol % of the A units are $R^1$.

The structure of the poly(orthoester) of the present invention, as shown in formula I, is one of alternating residues of a diketene acetal and a diol, with each adjacent pair of diketene acetal residues being separated by the residue of one polyol, preferably a diol.

In the presence of water, the α-hydroxy acid containing units are readily hydrolyzed at a body temperature of 37° C. and a physiological pH, to produce the corresponding hydroxy acids. These hydroxy acids then act as acidic catalysts to control the hydrolysis rate of the poly (orthoester) without the addition of exogenous acid. When the poly(orthoester) is used as a delivery vehicle or matrix entrapping an active agent, the hydrolysis of the poly (orthoester) causes release of the active agent.

Poly(orthoesters) having a higher mole percentage of the "α-hydroxy acid containing" units will have a higher rate of bioerodibility. Preferred poly(orthoesters) are those in which the mole percentage of the "α-hydroxy acid containing" units is in the range of about 1 to about 50 mole percent, more preferably from about 2 to about 30 mole percent, for example from about 5 to about 30 mole percent, especially from about 10 to about 30 mole percent.

Preferred poly(orthoesters) are those where:
  n is an integer of 5 to 1000;
  $R^5$ is hydrogen or methyl;
  $R^6$ is:

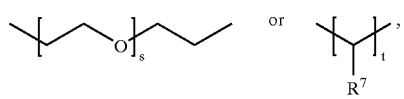

where s is an integer of 0 to 10, especially 1 to 4; s is an integer of 2 to 30, especially 2 to 10; and $R^7$ is hydrogen or methyl;
  $R^3$ is:

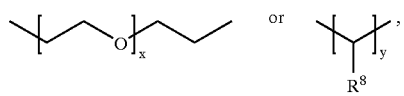

where x is an integer of 0 to 10, especially 1 to 4; y is an integer of 2 to 30, especially 2 to 10; and $R^8$ is hydrogen or methyl;
  $R^4$ is selected from the residues of aliphatic diols of 2 to 20 carbon atoms, preferably 2 to 10 carbon atoms, interrupted by one amide, include, urea, or urethane group; and
  the proportion of units in which A is $R^1$ is 1–50 mol %, preferably 2–30 mol %, more preferably 5–30 mol %.

While the presence of any of these preferences results in a poly(orthoester) that is more preferred than the same poly(orthoester) in which the preference is not met, the preferences are generally independent, and poly(orthoesters) in which a greater number of preferences is met will generally result in a poly(orthoester) that is more preferred than that in which a lesser number of preferences is met.

Expressed in terms of mole percent of the "hard" or "hydrogen bonding" unit relative to the poly(orthoester) as a whole, preferred poly(orthoesters) for liquid or ointment-like compositions are those in which the "hard" or "hydrogen bonding" unit constitutes about 20 mole percent or less. Likewise, preferred poly(orthoesters) for more solid compositions are those in which the "hard" or "hydrogen bonding" unit constitutes from about 60 mole percent to about 99.9 mole percent.

Poly(orthoesters) having a higher content of the "α-hydroxy acid containing" unit will have a higher rate of bioerodibility. Preferred poly(orthoesters) are those in which the "α-hydroxy acid containing" units constitute preferably from about 1 to about 50 mole percent, more preferably from about 2 to about 30 mole percent, for example from about 5 to about 30 mole percent, especially from about 10 to about 30 mole percent.

With respect to the individual "α-hydroxy acid containing" unit, p is preferably 1 to 6, more preferably 1 to 0.4, most preferably 1 or 2; $R^5$ is preferably hydrogen or methyl; and in the above definitions of $R^6$, s is preferably 2 to 12, more preferably 2 to 6 and most preferably 2; and t is preferably 4 to 12, more preferably 4 to 6 and most preferably 6.

With respect to the individual "hard" unit, HO—$R^2$—OH is preferably trans-cyclohexane-dimethanol.

With respect to the individual "soft" unit, in the definitions of $R^3$, x is preferably 2 to 12, more preferably 2 to 6 and most preferably 2; y is preferably 4 to 12, more preferably 4 to 6 and most preferably 6; $R^8$ is preferably hydrogen; $R^9$ and $R^{10}$ are preferably identical, more preferably an unbranched $C_4$–$C_{12}$ alkylene and most preferably an unbranched $C_6$–$C_{12}$ alkylene; $R^{11}$ is preferably hydrogen and $R^{12}$ is preferably methyl.

Preparation of the Poly(orthoesters)

The poly(orthoesters) are prepared according to the methods described in U.S. Pat. Nos. 4,549,010 and 5,968,543. Specifically, the poly(orthoesters) are prepared by the reaction of a diketene acetal of formula II:

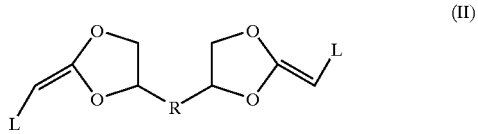

(II)

where L is hydrogen or a $C_{1-3}$ alkyl,
with a diol of the formula HO—$R^1$—OH, and optionally at least one diol of the formulae HO—$R^2$—OH, HO—$R^3$—OH, and HO—$R^4$—OH.

The rigidity or flexibility of the poly(orthoester) is determined by the proportions of the "hard" and "hydrogen bonding" units and "soft" units in the poly(orthoester) structure, with -greater rigidity achieved by including greater proportions of the "hard" and "hydrogen bonding" units in the poly(orthoester).

The bioerodibility of the poly(orthoester) is determined by the proportion of the hydrolysable α-hydroxy acid ester groups, with greater bioerodibility achieved by including greater proportions of the "α-hydroxy acid containing" units.

Thus, both characteristics of the resulting poly(orthoester) prepared from the reaction between the diketene acetal of Formula II and a mixture of the diols, are controlled by the ratio of quantities of the two to four types of diols in the diol mixture.

The preparation of the diketene acetals of formula ITI is disclosed in Crivello et al., *J. Polymer Sci., Par A: Polymer Chemistry*, 34, 3091–3102 (1996); and will be known to a person of ordinary skill in the art. A typical method is the condensation of a bis(diol) of formula III:

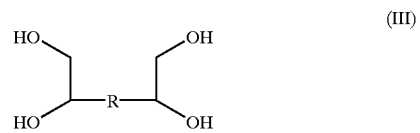

(III)

with two equivalents of a 2-halocarboxaldehyde dialkyl acetal, such as 2-bromoacetaldehyde diethyl acetal, followed by dehydrohalogenation to give the diketene acetal. The condensation of a glycol with diethylbromoacetals is described in Roberts et al., *J. Am. Chem. Soc.*, 80, 1247–1254 (1958), and dehydrohalogenation is described in Beyerstedt et al., *J. Am. Chem. Soc.*, 58, 529–553 (1936).

The diketene acetals may also be prepared by the isomerization of divinyl acetals. The isomerization of the double bond is described in Corey et al., *J. Org. Chem.*, 38, 3224 (1973). The divinyl acetals may be prepared by the condensation of the bis(diol) of formula III with two equivalents of a vinylic aldehyde, such as acrolein or crotonaldehyde, or their dialkyl acetals, such as acrolein dimethyl acetal, and such condensation reactions are well known. Thus, for example, 2,2'-divinyl-4,4'-bis(1,3-dioxolane) is prepared from the reaction of erythritol with acrolein in benzene/-p-toluenesulfonic acid; and is subsequently isomerized to 2,2'-diethylidene-4,4'-bis(1,3-dioxolane) with tris(triphenylphosphine)ruthenium(II) chloride.

The bis(diol) of formula III where R is a bond is erythritol. The bis(diol) of formula III where R is —$(CH_2)_a$— may be prepared by the oxidation of an a, -diene, such as 1,3-butadiene or 1,5-hexadiene, with an oxidizing reagent such as osmium tetroxide/hydrogen peroxide, or by other methods known in the art, to give the bis(diol). The bis(diol) of formula III where R is —$(CH_2)_b$—O—$(CH_2)_c$— may be prepared by the reaction of an ω-hydroxy-α-olefin, such as allyl alcohol, with an ω-haloalkyloxirane, such as epichlorohydrin, to form an ω-epoxy-β-olefin with the backbone interrupted by an oxygen atom, such as 2-allyloxymethyloxirane, which is then oxidized with an oxidizing reagent such as osmium tetroxide/hydrogen peroxide, or by other methods known in the art, to give the bis(diol).

The diols of the formulae HO—$R^1$—OH, HO—$R^2$—OH, HO—$R^3$—OH, and HO—$R^4$—OH are prepared according to methods known in the art, and as described, for example, in U.S. Pat. Nos. 4,549,010 and 5,968,543. Some of the diols are commercially available. The diol of the formula HO—$R^1$—OH that comprises a polyester moiety may be prepared by reacting a diol of the formula HO—$R^6$—OH with between 0.5 and 10 molar equivalents of a cyclic diester of an a-hydroxy acid, such as lactide or glycolide, and allowing the reaction to proceed at 100–200° C. for about 12 hours to about 48 hours. Although particular solvents are not required for this reaction, organic solvents such as dimethylacetamide, dimethyl sulfoxide, dimethylformamide, acetonitrile, pyrrolidone, tetrahydrofuran, and methylbutyl ether may be used. The preparation of diols in particular the diol of the formula HO—$R^3$—OH is generally disclosed in Heller et al., *J. Polymer Sci., Polymer Letters Ed.*, 18, 293–297 (1980), by reacting an appropriate divinyl ether with an excess of an appropriate diol. Diols of the formula HO—$R^4$—OH include diols where $R^4$ is R'CONR"R' (amide), R'CONR"COR' (imide), R'NR"CONR"R' (urea), and R'OCONR"R' (urethane), where each R' is independently an aliphatic, aromatic, or aromatic/aliphatic straight or branched chain hydrocarbyl, especially a straight or branched chain alkyl of 2 to 22 carbon atoms, especially 2 to 10 carbon atoms, and more especially 2 to 5 carbon atoms, and R" is hydrogen or $C_{1-6}$ alkyl, especially hydrogen or methyl, more especially hydrogen. Some representative diols of the formula HO—$R^4$—OH include N,N'-bis-(2-hydroxyethyl) terephthalamide, N,N'-bis-(2-hydroxyethyl) pyromellitic diimide, 1,1'-methylenedi(p-phenylene)bis-[3-(2-hydroxyethyl)-urea], N,N'-bis-(2-hydroxyethyl)oxamide, 1,3-bis(2-hydroxyethyl)urea, 3-hydroxy-N-(2-hydroxyethyl)-proplonamide, 4-hydroxy-N-(3-hydroxypropyl)butyramide, and bis(2-hydroxyethyl) ethylenedicarbamate. These diols are known to the art in reported syntheses and may are commercially available. Representative diols of the formula HO—$(CH_2)_n$—NHCO—$(CH_2)_m$—OH where n is an integer of 2 to 6 and m is an integer of 2 to 5 are made by the reaction of 2-aminoethanol, 3-aminopropanol, 4-aminobutanol, 5-aminopentanol, or 6-aminohexanol with β-propiolactone, γ-butyrolactone, δ-valerolactone, or ε-caprolactone. Representative diols of the formula HO—$(CH_2)_n$—NHCOO—$(CH_2)_m$—OH. where n and m are each integers of 2 to 6 are made by the reaction of the same aminoalcohol just mentioned with cyclic carbonates of the formula

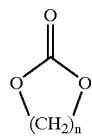

such as ethylene carbonate. Bis-amide diols of the formula HO—A—NHCO—B—CONH—A—OH are prepared by the reaction of a diacid, optionally in activated form, such as the diacyldihalide, with two equivalents of a hydroxy-amine. Other methods of preparation of the diols of the formula HO—$R^4$—OH are known in the art.

Once made, the diol of the formula HO—$R^1$—OH, and the diol(s) of the formulae HO—$R^2$—OH, HO—$R^3$—OH, and HO—$R^4$—OH in the desired proportions are mixed with the diketene acetal of formula II, typically in a slightly less than 1:1 (e.g. 0.5:1–0.9:1) ratio of total number of moles of diketene acetal to total number of moles of diols, in a suitable solvent at ambient temperature. The condensation reaction between the diketene acetal and the diols is carried out under conditions which are described in, for example, U.S. Pat. Nos. 4,304,767, 4,549,010, and 5,968,543, and are well known to those skilled in the art; and will also be readily apparent from the structures of the reactants themselves. Suitable solvents are aprotic solvents, such as dimethylacetamide, dimethyl sulfoxide, dimethylformamide, acetonitrile, acetone, ethyl acetate, pyrrolidone, tetrahydrofuran, and methylbutyl ether, and the like. Catalysts are not required for this reaction, but when used, suitable catalysts are iodine in pyridine, p-toluenesulfonic acid; salicylic acid, Lewis acids (such as boron trichloride, boron trifluoride, boron trichloride etherate, boron trifluoride etherate, stannic oxychloride, phosphorous oxychloride, zinc chloride, phosphorus pentachloride, antimony pentafluoride, stannous octoate, stannic chloride, diethyl zinc, and mixtures thereof); and Bronsted catalysts (such as polyphosphoric acid, crosslinked polystyrene sulfonic acid, acidic silica gel, and mixtures thereof). A typical amount of catalyst used is about 0.2% by weight relative to the diketene acetal. Smaller or larger amounts can also be used, such as 0.005% to about 2.0% by weight relative to the diketene acetal. Once the reaction is complete, the reaction mixture is allowed to cool and concentrated by rotoevaporation under vacuum. The concentrated mixture may be further dried under vacuum at an elevated temperature.

The poly(orthoesters) may also be prepared by reaction of the diketene acetal with the chosen diol(s) under similar reaction conditions, but in the presence of a "chain stopper" (a reagent that terminates poly(orthoester) chain formation). Suitable chain stoppers are $C_{5-20}$ alkanols, especially $C_{10-20}$ alkanols. The chain stopper is preferably present in from 1–20 mol % based on the diketene acetal. The poly (orthoesters) thus prepared have lower molecular weights with a lower molecular weight dispersion than those prepared by the reaction of the diketene acetals with only diols.

The invention includes poly(orthoesters) which contain all four types of units as well as poly(orthoesters) containing from only the "α-hydroxy acid containing" units, or a mixture of these units with only one or two of the "hard", "soft", and "hydrogen bonding" units. It also includes poly (orthoesters) prepared from a mixture of units which contains two or more diols of the same type.

It is also understood that the present invention encompasses cross-linked poly(orthoesters) which are prepared by employing one or more polyols having more than two hydroxy functional groups. Such cross-linked poly (orthoesters) may be prepared preferably by first reacting the diketene acetal with a mixture of diols comprising a diol of the formula HO—RI—OH and optionally at least one diol of the formulae HO—$R^2$—OH, HO—$R^3$—OH, and HO—$R^4$—OH, followed by addition of the polyol(s) having more than two hydroxy functional groups. Alternatively, the polyol(s) having more than two hydroxy functional groups may be added simultaneously with the diol of the formula HO—$R^1$—OH and other diols. Polyols having more than two hydroxy functional groups suitable for the preparation of the cross-linked poly(orthoesters) may be the straight or branched chain type, including polyhydroxyl compounds such as 1,2,3-propanetriol, 1,2,5-pentanetriol, 1,2,6-hexanetriol, 1,3,5-pentanetriol, 1,2,4-butanetriol, 1,4,7-heptanetriol, 1,5,10-decanetriol, 1,5,12-dodecanetriol, 1,2,3, 4,5,6-hexane-hexol and the like. Other representative polyols of the type are described in U.S. Pat. No. 4,304,767. The reaction conditions (e.g., suitable solvents and reaction temperatures) and procedures for the preparation of the cross-linked poly(orthoesters) are similar to those described above for the preparation of the poly(orthoesters) employing only the diols, and are also described in U.S. Pat. Nos. 4,304,767 and 5,968,543.

Uses of the Poly(Orthoesters)

The present poly(orthoesters) can be used for any use in which bioerodible polymers are usable, such as vehicles for the sustained release of an active agent or as orthopedic implants.

To use the poly(orthoester) as a sustained-release vehicle, the active agent must be incorporated into a matrix of the poly(orthoester) or encapsulated within a capsule (or a "microcapsule" or "nanocapsule", as those terms are sometimes used) of the poly(orthoester). Methods for the preparation of sustained-release dosage forms using biodegradable polymers are well known in the art, as discussed in the references cited in the "Description of the Prior Art" section of this application, and in other references familiar to those of ordinary skill in the art; so that a person of ordinary skill in the art would have no difficulty, having regard to that skill and this disclosure, in preparing sustained-release formulations using the poly(orthoester) of this invention. Suitable active agents include therapeutic agents such as pharmaceutical or pharmacological active agents, e.g. drugs and medicaments, as well as prophylactic agents, diagnostic agents, and other chemicals or materials useful in preventing or treating disease. The compositions of this invention are particularly useful for the therapeutic treatment of humans and other mammals, but may also be used for other animals. In addition, the sustained-release compositions of this invention may also be used for the release of cosmetic and agricultural agents, or for the release of biocides, such as fungicides or other pesticides, into an environment where prolonged release of the active agent is desired.

In the case of matrix formulations, the poly(orthoester) is first mixed with the active agent. High homogeneity may be achieved by mixing the poly(orthoester) in its heat softened state with the active agent, followed by lowering the temperature to harden the composition. Alternatively, the poly (orthoester) can be dissolved in an appropriate casting solvent, such as tetrahydrofuran, methylene chloride, chloroform or ethyl acetate, and the active agent can then be dispersed or dissolved in the poly(orthoester) solution, followed by evaporating the solvent to achieve the finished composition. Another method is grinding a solid poly (orthoester) material into powder which is then mixed with a powdered active agent. The active agent may also be incorporated into the mixture of monomers before polymerization provided that it is stable under the polymerization conditions and does not interfere with the polymerization reaction.

If the active agent is one that is unstable at elevated temperatures (e.g. above 40° C.), or in the presence of organic solvents or organic solvent/water mixtures, such as a protein, then special preparation techniques may be required to minimize the exposure of the active agent to damaging conditions. Such techniques are disclosed in, for example, U.S. Pat. No. 5,620,697 (Törmälä et al., assigned to Orion-Yhtyma Oy and Leiras Oy), which discloses ultrasonic melting to form matrix-type pharmaceutical compositions, and U.S. Pat. No. 5,518,730 Fuisz, assigned to Fuisz Technologies, Inc.), which discloses melt-spinning, both of which techniques are designed to minimize the exposure of the polymer and active to elevated temperatures. Other methods are disclosed in the patents and literature references cited elsewhere in this application.

An alternate method for the incorporation and release of sensitive therapeutic agents is to use bioerodible poly (orthoesters) that have physical properties tailored for this incorporation. For example, the poly(orthoester) may be chosen so that it is semi-solid and has an ointment-like consistency, rather than being fully solid. Thus, a poly (orthoester) may be chosen that has a very high viscosity at normal body temperature of 37° C. so that little if any deformation takes place at that temperature. However, the viscosity of the poly(orthoester) may decrease substantially at temperatures no higher than 45° C., or preferably by 40° C., so that injection of the material may be possible at a temperature at which the active agent retains its activity.

The composition obtained from any of the above methods can be readily processed into a variety of shapes and forms for implantation, insertion or placement on the body or into body cavities or passageways. For example, the poly (orthoester) composition may be injection molded, extruded or compressed into a thin film or made into devices of various geometric shapes or forms such as flat, square, round, cylindrical, tubular, disc, ring and the like. Rod- or pellet-shaped devices may be implanted through a trocar, such as is known for Norplant® implants, and these or other shapes may be implanted by minor surgical procedures. Alternatively, a device may be implanted following a major surgical procedure such as tumor removal in the surgical treatment of cancer.

The poly(orthoester) composition may also be injected by syringe subcutaneously or intramuscularly as particles of $0.1\mu$ to $1000\mu$, preferably $0.5\mu$ to $200\mu$, and more preferably $1\mu$ to $150\mu$ suspended in a pharmaceutically acceptable injection base. Liquid vehicles useful for suspending the drug-poly(orthoester) composition for injection include isotonic saline solution or oils (such as corn oil, cottonseed oil, peanut oil and sesame oil) which, if desired, may contain other adjuvants.

Another injectable dosage form may be prepared from an active agent mixed in with a poly(orthoester) of the present invention which has an ointment-like consistency. Such a dosage form may be administered by injection with or without a solvent.

The poly(orthoester) composition administered by either injection or implantation undergoes bioerosion m the body into non-toxic and non-reactive materials. By controlling the number of hydrolysable bonds in the poly(orthoester), the active agent may be released at a desired rate. Implants prepared from the present poly(orthoesters) in which the poly(orthoester) constitutes the matrix containing an active agent also have the advantage that they do not require removal because of the bioerodibility of the poly (orthoester).

In some cases, particles with cores of the pure active agent coated with various thicknesses of the present poly (orthoester) may be preferred for sustained delivery of the active agent. Coating or encapsulation of discrete particles of the active agent may be accomplished by conventional methods which are all well-known to the person skilled in the art. For example, finely divided drug particles may be suspended in a solvent system (in which the drug is not soluble) containing the dissolved poly(orthoester) and other excipients, followed by spray drying. Alternatively, the drug particles may be placed in a rotating pan or a fluid-bed dryer and the poly(orthoester) dissolved in a carrier solvent is sprayed onto the drug particles until a suitable coating quantity is deposited on the particles to give a desired thickness. The coating may also be achieved by suspending the drug particles in a solvent system containing the dissolved poly(orthoester) followed by adding-to the suspension a non-solvent causing the poly(orthoester) to precipitate and form a coating over the drug particles.

For the sustained release compositions, because the active agent will be released over a controlled period of time, the agent usually is present in an amount which is greater than the conventional single dose. The relative proportions of the active agent and the poly(orthoester) can vary over a wide range (e.g., 0.1 to 50 weight percent) depending on the therapeutic agent and the desired effect.

Sustained compositions of cosmetic and agricultural agents may also be prepared by any one of the methods as described above, using the poly(orthoesters) of the present invention.

The solid poly(orthoesters) (those containing a high percentage of the "hard" unit and/or a high proportion of the "hydrogen bonding" unit) are also useful for a variety of orthopedic applications. For example, they can be used as fracture fixation devices for repair of osteochondral defects, ligament and tendon reconstructions and bone substitutes. In addition, the fact that the present poly(orthoesters) permit simultaneous selection of both a desired level of their mechano-physical state and a desired rate of bioerodibility, also renders them attractive as grafts or scaffolds on which cells can be cultured in vitro prior to implantation to regenerate tissues. Tissues which can be regenerated using this approach include but not limited to, bone, tendon, cartilage, ligaments, liver, intestine, ureter and skin tissues. For example, the poly(orthoesters) may be used to regenerate skin for patients with burns or skin ulcers. Cartilages may be repaired by first isolating chondrocytes from a patient (or a donor), allowing them to proliferate on the scaffolds prepared from the present poly(orthoester) and re-implanting the cells in the patient.

The poly(orthoester) scaffolds or implants may further contain other biologically active substances or synthetic inorganic materials such as reinforcing filler material for enhancing the mechanical properties of the scaffolds or implants (e.g. calcium sodium metaphosphate fibers), antibiotics or bone growth factors to induce and/or promote orthopedic restoration and tissue regeneration.

The compositions are also stable. The release rates of the active agent are not affected by irradiation for sterilization.

Particular Compositions and their Uses

Exemplary compositions of this invention, and their uses, include:

(1) compositions containing local anesthetics, optionally in combination with glucocorticosteroids such as dexamethasone, cortisone, hydrocortisone, prednisone, prednisolone, beclomethasone, betamethasone, flunisolide, fluoconolone acetonide, fluocinonide, triamcinolone, and the like, for the prolonged relief of local pain or a prolonged nerve blockade. This use is discussed further below;

(2) compositions containing cancer chemotherapeutic agents, such as those listed above under "Active Agents", for deposition by syringe or by injection into tumors or operative sites from which a tumor has been ablated, for tumor control or treatment and/or the suppression of regrowth of the tumor from residual tumor cells after ablation of the tumor;

(3) compositions containing progestogens, such as flurogestone, medroxyprogesterone, norgestrel, norgestimate, norethindrone, and the like, for estrus synchronization or contraception;

(4) compositions containing antimetabolites such as fluorouracil and the like, as an adjunct to glaucoma filtering surgery; compositions containing antiangiogenic agents such as combrestatin, for the treatment of macular degeneration and retinal angiogenesis; and other compositions for the controlled release of ophthalmic drugs to the eye;

(5) compositions containing therapeutic polypeptides (proteins), such as insulin, LHRH antagonists, and the like, for the controlled delivery of these polypeptides, avoiding the need for daily or other frequent injection;

(6) compositions containing anti-inflammatory agents such as the NSAIDs, e.g. ibuprofen, naproxen, COX-1 or COX-2 inhibitors, and the like, or glucocorticosteroids, for intra-articular injection;

(7) compositions containing antibiotics, for the prevention or treatment of infection, especially for deposition into surgical sites to suppress post-operative infection, or into or on wounds, for the suppression of infection (e.g. from foreign bodies in the wound);

(8) compositions containing morphogenic proteins such as bone morphogenic protein; and (9) compositions containing DNA or other polynucleotides, such as antisense oligonucleotides.

Delivery of Controlled-release Local Anesthetics by Injection

Local anesthetics induce a temporary nerve conduction block and provide pain relief which lasts from a few minutes to a few hours. They are frequently used to prevent pain in surgical procedures, dental manipulations or injuries.

The synthetic local anesthetics may be divided into two groups: the slightly soluble compounds and the soluble compounds. Conventionally, the soluble local anesthetics can be applied topically and by injection, and the slightly soluble local anesthetics are used only for surface application. The local anesthetics conventionally administered by injection can also be divided into two groups, esters and non-esters. The esters include (1) benzoic acid esters (piperocaine, meprylcaine and isobucaine); (2) para-aminobenzoic acid esters (procaine, tetracaine, butethamine, propoxycaine, chloroprocaine); (3) meta-aminobenzoic acid esters (metabutethamine, primacaine); and (4) para-ethoxy-benzoic acid ester (parethoxycaine). The non-esters are amides (amides or nonesters) which include bupivacaine, lidocaine, mepivacaine, pyrrocaine and prilocaine.

Many of the local anesthetics are conventionally used in the form of their acid addition salts, as this provides solubility in aqueous injection media. However, because the presence of the large amount of acid within such a local anesthetic acid addition salt will result in more rapid degradation of the poly(orthoesters) and release of the local anesthetic, it is generally desirable to use the local anesthetics in free base form, or with only a small proportion of the acid addition salt present (addition of small quantities of the acid addition salt may provide enhanced release if desired).

The semi-solid injectable form of a local anesthetic of the present invention is prepared by incorporating the local anesthetic into the delivery vehicle in a manner as described above. The concentration of the local anesthetic may vary from 1–60 wt. %, preferably 5–30 wt. %, e.g. about 10 wt. %. The semi-solid composition is then filled into a syringe with a 18–25 gauge needle, and injected into sites that are painful or to be subjected to surgical procedures. The semi-solid injectable composition of the present invention can be used for controlled delivery of both slightly soluble and soluble local anesthetics.

Because the duration of action of a local anesthetic is proportional to the time during which it is in actual contact with nervous tissues, the present injectable delivery system can maintain localization of the anesthetic at the nerve for an extended period of time which will greatly prolong the effect of the anesthetic.

A number of authors, including Berde et al., U.S. Pat. No. 6,046,187 and related patents, have suggested that the co-administration of a glucocorticosteroid may prolong or otherwise enhance the effect of local anesthetics, especially controlled-release local anesthetics; and formulations containing a local anesthetic and a glucocorticosteroid, and their uses for controlled release local anesthesia, are within the scope of this invention.

EXAMPLE

The following synthesis illustrates the preparation of a poly(orthoester) of this invention.

The poly(orthoester) in this example is prepared from 2,2'-diethylidene-4,4'-bis(1,3-dioxolane), a diol of formula IV:

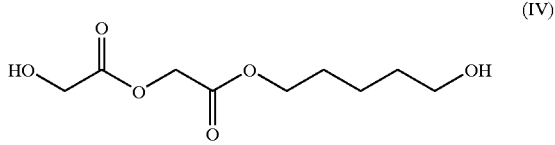

(IV)

trans-cyclohexanedimethanol (t-CDM), and N,N'-bis(2-hydroxyethyl)oxamide. The molar ratio of the four components (2,2'-diethylidene-4,4'-bis(1,3-dioxolane):diol of formula IV:t-CDM:-N,N'-bis(2-hydroxyethyl)oxamide is 100:9:90:1.

2,2'-Diethylidene-4,4'-bis(1,3-dioxolane) is prepared as described in Crivello et al., referred to above; the diol of formula IV is prepared as described in U.S. Pat. No. 5,968,543; and t-CDM and N,N'-bis(2-hydroxyethyl)oxamide are obtained commercially.

Under rigorously anhydrous conditions, 2,2'-diethylidene-4,4'-bis(1,3-dioxolane) (40 mmol), diol of formula IV (3.6 mmol), t-CDM (36 mmol), and 4-hydroxy-N-(3-hydroxypropyl)butyramide (0.4 mmol) are weighed into a 250 mL round bottom flask, and the mixture dissolved in anhydrous tetrahydrofuran (75 mL). To this solution is added a p-toluenesulfonic acid solution in tetrahydrofuran (5 drops, 40 mg/mL) to initiate the polymerization. The solution comes to a boil within a few minutes. The solution is allowed to cool to room temperature, then is slowly poured with vigorous stirring in to an excess of methanol (800 mL) containing triethylamine (1 mL) as a stabilizer. The precipitated poly(orthoester) is collected and dried overnight in a vacuum oven at 40° C.

The foregoing is offered primarily for purposes of illustration. It will be readily apparent to those skilled in the art that the molecular structures, proportions of the reactant materials, methods of use and other parameters of the invention described herein may be further modified or substituted in various ways without departing from the spirit and scope of the invention.

What is claimed is:

1. A pharmaceutical composition comprising:

(a) an active agent; and
   (b) as a vehicle, a poly(orthoester) that is the product of a reaction between:
      (i) a diketene acetal of formula II:

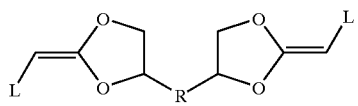

(II)

where:

R is a bond, —$(CH_2)_a$—, or —$(CH_2)_b$—O—$(CH_2)_c$—; where a is an integer of 1 to 10, and b and c are independently integers of 1 to 5; and L is hydrogen or a $C_{1-3}$ alkyl, and (ii) a polyol or mixture of polyols in which at least 0.1 mole percent of the total polyol content is a diol of the formula HO—$R^1$—OH, where $R^1$ is:

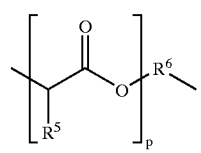

where:

p is an integer of 1 to 20;

$R^5$ is hydrogen or $C_{1-4}$ alkyl; and $R^6$ is:

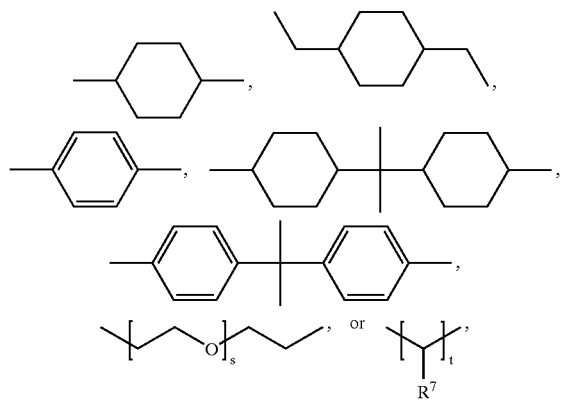

where:

s is an integer of 0 to 30;

t is an integer of 2 to 200; and $R^7$ is hydrogen or $C_{1-4}$ alkyl.

2. The composition of claim 1 where the poly(orthoester) is of formula I:

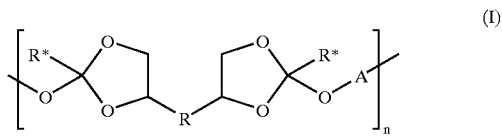

(I)

where:

R is a bond, —$(CH_2)_a$—, or —$(CH_2)_b$—O—$(CH_2)_c$—; where a is an integer of 1 to 10, and b and c are independently integers of 1 to 5;

$R^*$ is a $C_{1-4}$ alkyl;

n is an integer of at least 5; and

A is $R^1$, $R^2$, $R^3$, or $R^4$, where $R^1$ is:

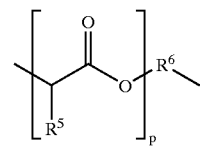

where:

p is an integer of 1 to 20;

$R^5$ is hydrogen or $C_{1-4}$ alkyl; and $R^6$ is

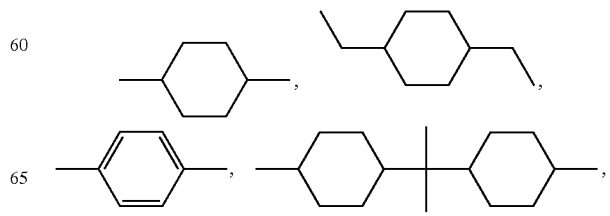

-continued

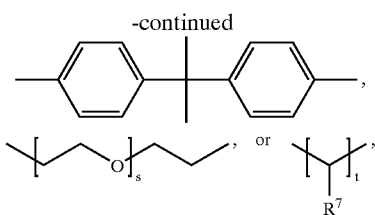

where:
s is an integer of 0 to 30;
t is an integer of 2 to 200; and
$R^7$ is hydrogen or $C_{1-4}$ alkyl;
$R^2$ is:

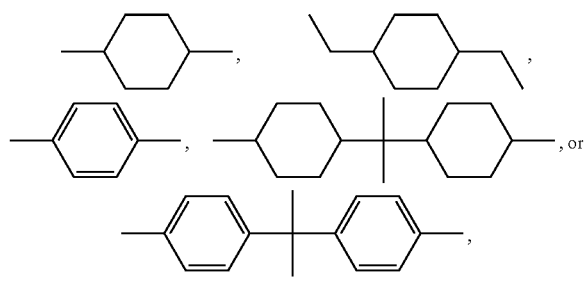

$R^3$ is:

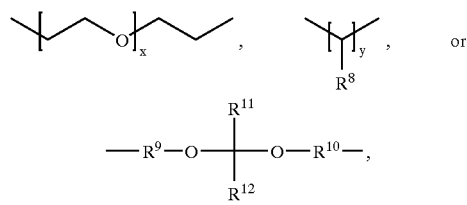

where:
x is an integer of 0 to 30;
y is an integer of 2 to 200;
$R^8$ is hydrogen or $C_{1-4}$ alkyl;
$R^9$ and $R^{10}$ are independently $C_{1-12}$ alkylene;
$R^{11}$ is hydrogen or $C_{1-6}$ alkyl and $R^{12}$ is $C_{1-6}$ alkyl; or $R^{11}$ and $R^{12}$ together are $C_{3-10}$ alkylene; and
$R^4$ is the residue of a diol containing at least one functional group independently selected from amide, imide, urea, and urethane groups;
in which at least 0.1 mol % of the A units are $R^1$.

3. The composition of claim 2 where n is about 5 to about 1000.

4. The composition of claim 2 where the poly(orthoester) comprises about 1 to about 50 mole percent of units in which A is $R^1$.

5. The composition of claim 2 where p is 1 to 2.

6. The composition of claim 2 where $R^5$ is hydrogen or methyl.

7. The composition of claim 2 where the poly(orthoester) comprises up to about 20 mole percent of units in which A is $R^2$.

8. The composition of claim 2 where the poly(orthoester) comprises about 60 to about 99.9 mole percent of units in which A is $R^2$.

9. The pharmaceutical composition of claim 1 where the fraction of the active agent is from 1% to 60% by weight of the composition.

10. The pharmaceutical composition of claim 9 where the fraction of the active agent is from 5% to 30% by weight of the composition.

11. The pharmaceutical composition of claim 9 where the active agent is selected from anti-infectives, antiseptics, steroids, therapeutic polypeptides, anti-inflammatory agents, cancer chemotherapeutic agents, narcotics, local anesthetics, antiangiogenic agents, vaccines, antigens, DNA, and antisense oligonucleotides.

12. The pharmaceutical composition of claim 11 where the active agent is a therapeutic polypeptide.

13. The pharmaceutical composition of claim 11 where the active agent is a local anesthetic.

14. The pharmaceutical composition of claim 13 further comprising a glucocorticosteroid.

15. The pharmaceutical composition of claim 11 where the active agent is an antiangiogenic agent.

16. A method of treating a disease state treatable by controlled release local administration of an active agent, comprising locally administering a therapeutically effective amount of the active agent in the form of a pharmaceutical composition of claim 1.

17. The method of claim 16 where the active agent is selected from anti-infectives, antiseptics, steroids, therapeutic polypeptides, anti-inflammatory agents, cancer chemotherapeutic agents, narcotics, local anesthetics, antiangiogenic agents, vaccines, antigens, DNA, and antisense oligonucleotides.

18. A method of preventing or relieving local pain at a site in a mammal, comprising administering to the site a therapeutically effective amount of a local anesthetic in the form of a pharmaceutically acceptable composition of claim 1.

19. A device for orthopedic restoration or tissue regeneration comprising a poly(orthoester) that is the product of a reaction between:

(i) a diketene acetal of formula II:

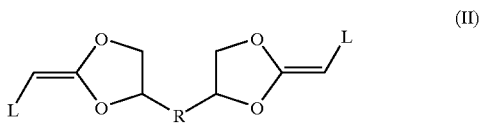

(II)

where:
R is a bond, —$(CH_2)_a$—, or —$(CH_2)_b$—O—$(CH_2)_c$—; where a is an integer of 1 to 10, and b and c are independently integers of 1 to 5; and
L is hydrogen or a $C_{1-3}$ alkyl, and (ii) a polyol or mixture of polyols in which at least 0.1 mole percent of the total polyol content is a diol of the formula HO—$R^1$—OH, where
$R^1$ is:

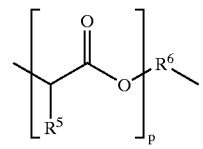

where:
p is an integer of 1 to 20;
$R^5$ is hydrogen or $C_{1-4}$ alkyl; and $R^6$ is:

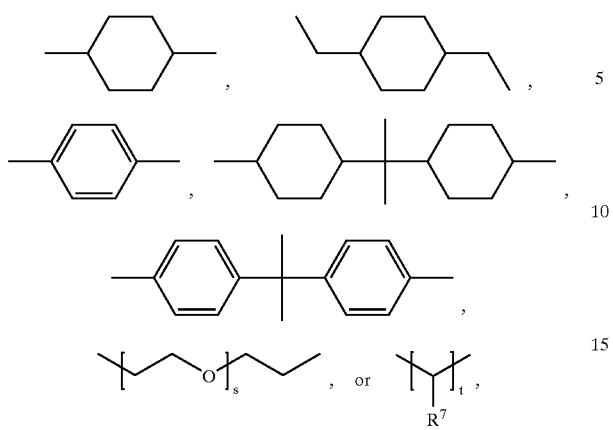

where:
s is an integer of 0 to 30;
t is an integer of 2 to 200; and
$R^7$ is hydrogen or $C_{1-4}$ alkyl.

20. A bioerodible implant comprising a poly(orthoester) that is the product of a reaction between:

(i) a diketene acetal of formula II:

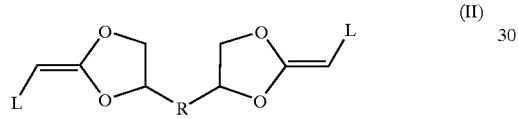

(II)

where:
R is a bond, $-(CH_2)_a-$, or $-(CH_2)_b-O-(CH_2)_c-$; where a is an integer of 1 to 10, and b and c are independently integers of 1 to 5; and
L is hydrogen or a $C_{1-3}$ alkyl, and (ii) a polyol or mixture of polyols in which at least 0.1 mole percent of the total polyol content is a diol of the formula HO—$R^1$—OH, where
$R^1$ is:

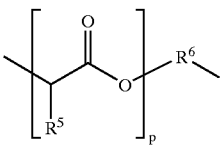

where:
p is an integer of 1 to 20;
$R^5$ is hydrogen or $C_{1-4}$ alkyl; and
$R^6$ is:

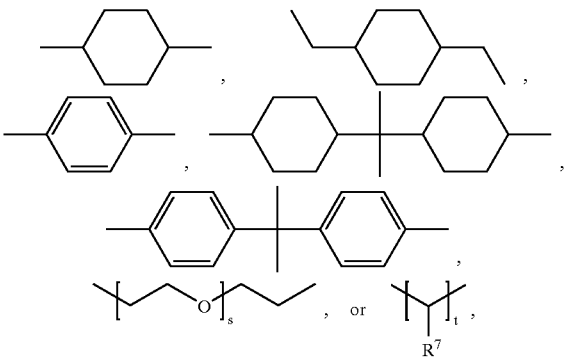

where:
s is an integer of 0 to 30;
t is an integer of 2 to 200; and
$R^7$ is hydrogen or $C_{1-4}$ alkyl.

* * * * *